(12) United States Patent
Bonomi et al.

(10) Patent No.: US 9,955,916 B2
(45) Date of Patent: May 1, 2018

(54) METHOD AND APPARATUS FOR ESTIMATING THE FLUID CONTENT OF A PART OF THE BODY OF A SUBJECT

(71) Applicant: KONINKLIJKE PHILIPS N.V., Eindhoven (NL)

(72) Inventors: Alberto Giovanni Bonomi, Eindhoven (NL); Jennifer Caffarel, Eindhoven (NL); Illapha Gustav Lars Cuba Gyllensten, Stockholm (SE); Jarno Mikael Riistama, Waalre (NL); Harald Reiter, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 170 days.

(21) Appl. No.: 14/405,802

(22) PCT Filed: Jun. 4, 2013

(86) PCT No.: PCT/IB2013/054592
§ 371 (c)(1),
(2) Date: Dec. 5, 2014

(87) PCT Pub. No.: WO2013/182985
PCT Pub. Date: Dec. 12, 2013

(65) Prior Publication Data
US 2016/0029953 A1    Feb. 4, 2016

Related U.S. Application Data

(60) Provisional application No. 61/657,217, filed on Jun. 8, 2012.

(51) Int. Cl.
*A61B 5/05* (2006.01)
*A61B 5/00* (2006.01)
(Continued)

(52) U.S. Cl.
CPC .......... *A61B 5/4878* (2013.01); *A61B 5/0537* (2013.01); *A61B 5/0809* (2013.01);
(Continued)

(58) Field of Classification Search
CPC ...... A61B 5/0537; A61B 5/053; A61B 5/4872
(Continued)

(56) References Cited

U.S. PATENT DOCUMENTS

| | | |
|---|---|---|
| 4,008,712 A | 2/1977 | Nyboer |
| 5,282,840 A | 2/1994 | Hudrlik |

(Continued)

FOREIGN PATENT DOCUMENTS

| | | |
|---|---|---|
| JP | 2012030033 A | 2/2012 |
| WO | 2005027717 A2 | 3/2005 |
| WO | 2009125327 A1 | 10/2009 |
| WO | 2010038176 A1 | 4/2010 |
| WO | 2012051261 A2 | 4/2012 |

OTHER PUBLICATIONS

Beckmann et al: "Optimal Electrode Placement and Frequency Range Selection for the Detection of Lung Water Using Bioimpedance Spectroscopy"; Proceedings of the 29th Annual International Conference of the IEEE EMBS, Aug. 2007, pp. 2685-2688.

(Continued)

*Primary Examiner* — Daniel Cerioni

(57) ABSTRACT

There is provided a method for estimating the volume of fluid in part of the body of a subject, the method comprising obtaining a measurement of the circumference, c, of the part of the body of the subject; obtaining a measurement of the impedance of the part of the body of the subject using electrodes attached across the part of the body of the subject; and estimating the volume of fluid in the part of the body of the subject from the measurement of impedance and the measurement of the circumference c. An apparatus comprising a control unit configured to perform the method is also provided.

20 Claims, 3 Drawing Sheets

(51) Int. Cl.
    *A61B 5/053* (2006.01)
    *A61B 5/08* (2006.01)
(52) U.S. Cl.
    CPC .......... *A61B 5/4875* (2013.01); *A61B 5/4881* (2013.01); *A61B 5/6823* (2013.01); *A61B 5/7278* (2013.01); *A61B 2562/0214* (2013.01)
(58) Field of Classification Search
    USPC ........................................................ 600/547
    See application file for complete search history.

(56) References Cited

U.S. PATENT DOCUMENTS

| | | | |
|---|---|---|---|
| 5,788,643 | A | 8/1998 | Feldman |
| 2002/0123674 | A1* | 9/2002 | Plicchi ................. A61B 5/0084 600/300 |
| 2003/0120170 | A1 | 6/2003 | Zhu et al. |
| 2005/0215918 | A1 | 9/2005 | Frantz et al. |
| 2006/0258952 | A1* | 11/2006 | Stahmann ............ A61B 5/0537 600/547 |
| 2008/0027349 | A1 | 1/2008 | Stylos |
| 2010/0106046 | A1 | 4/2010 | Shochat et al. |
| 2011/0054271 | A1 | 3/2011 | Derchak et al. |
| 2013/0096456 | A1 | 4/2013 | Fukuda et al. |

OTHER PUBLICATIONS

De Lorenzo et al: "Predicting Body Cell Mass With Bioimpedance by Using Theoretical Methods: A Technological Review";Jourlnal App. Physiol, 1997, pp. 1542-1558.

Fenech et al: "Extracellular and Intracellular Volume Variations During Postural Change Measured by Segmental and Wrist-Ankle Bioimpedance Spectroscopy"; IEEE Transactions on Biomedical Engineering, vol. 51, No. 1, Jan. 2004, pp. 166-175.

Hanai et al : "Dielectric Properties of Emulsions II"; Colloid & Polymer Science, vol. 171, No. 1, 1960, pp. 20-23.

Hoffer et al: "Correlation of Whole-Body Impedance With Total Body Water Volume"; Journal of Applied Physiology, vol. 27, No. 4, Oct. 1969, pp. 531-534.

Jaffrin et al: "Body Fluid vol. Measurements by Impedance: A Review of Bioimpedance Spectroscopy (BIS) and Bioimpedance Analysis (BIA) Methods"; Medical Engineering & Physics 30, 2008, pp. 1257-1269.

Merritt: "Electronic Textile-Based Sensors and Systems for Long-Term Health Monitoring"; Dissertation Submitted to North Carolina State University, Mar. 2008, 175 Page Document.

Raaijmakers et al: "Estimation of Non-Cardiogenic Pulmonary Oedema Using Dual-Frequency Electrical Impedance"; Med. Biol. Eng. Compt., 1998, 36, pp. 461-466.

* cited by examiner

METHOD AND APPARATUS FOR ESTIMATING THE FLUID CONTENT OF A PART OF THE BODY OF A SUBJECT

CROSS-REFERENCE TO PRIOR APPLICATIONS

This application is the U.S. National Phase application under 35 U.S.C. § 371 of International Application Serial No. PCT/IB2013/054592, filed on Jun. 4, 2013, which claims the benefit of U.S. Application Ser. No. 61/657,217, filed on Jun. 5, 2012. These applications are hereby incorporated by reference herein.

TECHNICAL FIELD OF THE INVENTION

The invention relates a method and apparatus for estimating the fluid content of part of the body of a subject, and in particular relates to a method and apparatus for estimating the fluid content of part of the body of the subject (for example their lungs) from bio-impedance measurements.

BACKGROUND TO THE INVENTION

Pulmonary oedema is a clinical condition that is caused by a number of different diseases such as heart failure or kidney diseases. It consists of an accumulation of fluid in the interstitial and alveolar space of the lung following increased blood pressure in the pulmonary capillary vessels that lead to leakage of water from the blood to the lung space. This condition has a progressive nature and clinical signs of pulmonary oedema occur late, typically when the lung fluid has increased at least six-fold from the initial stage of interstitial oedema. This means that pulmonary oedema is often not detected early, and necessary treatment for the patient is delayed.

Existing clinical methods to detect pulmonary oedema are invasive and expensive, such as chest radiography or pulmonary capillary wedge-pressure measurements. Pre-clinical detection and monitoring of lung fluid volume would enhance medical treatment and potentially reduce medical costs resulting from hospitalization of a patient with pulmonary oedema.

Bio-impedance spectroscopy (BIS) is a low-cost and non-invasive technique for detecting pulmonary oedema. The principle underlying this technique is the fact that the electrical impedance (resistance and reactance) of the biological tissue is directly linked to the hydration and water content of the tissue, namely intra-cellular and extra-cellular water. Therefore, measurements of the electrical properties of the tissue can indicate the amount of fluid present that part of the body. The BIS method has been used to determine the total amount of water in the body and body composition (i.e. fat and fat free mass). Recently, BIS has been used to monitor the accumulation of fluid as an indicator for pulmonary oedema using whole-body, intra-thoracic or trans-thoracic measurement systems.

Intra-thoracic and trans-thoracic BIS provide a more sensitive and direct measure of pulmonary fluid content than whole-body techniques, which detect fluid accumulation in both peripheral and pulmonary regions. However, thoracic BIS measurements can only currently be used to generate qualitative assessments of changes in lung fluid content over time, which can indicate the onset of pulmonary oedema, and it is not yet possible to use these measurements to quantify the amount of fluid in the lungs nor to quantify the change in lung fluid content.

Therefore, there is a need for an improved method and apparatus for estimating the fluid content of the lungs from bio-impedance measurements that can provide quantitative indications of the amount of fluid in the lungs and/or the change in lung fluid content. Such a method and apparatus could be used in a monitoring system to detect the presence and progression of pulmonary oedema, as well as monitoring improvements in the patient's condition as a result of receiving treatment.

SUMMARY OF THE INVENTION

Trans-thoracic bio-impedance measurements are performed by measuring electrical properties (in particular the impedance) of the biological tissue using electrodes placed on the skin in the chest area. As body fluids have a higher conductivity than air, fat, lung tissue and connecting tissue present in the thorax, high fluid content in the lungs leads to a reduction in the measured impedance. In addition, the impedance of the biological tissue is not only determined by its composition (or amount of water) but also the shape and size of the measured volume.

It has been found that trans-thoracic BIS measurements are strongly associated with the cross-sectional area of the chest of the subject, with larger chest circumferences (and therefore a larger cross-sectional area) leading to higher measured impedances. This has been found to be the case even when the spacing between the electrodes placed across the chest is consistent between different subjects. The graph in FIG. 1 plots chest circumference (measured in centimeters, cm) against the resistance of the extra-cellular space $R_{EXT}$, (which is the external resistance from the Cole-Cole model of biological tissue impedance as described in "Predicting body cell mass with bioimpedance by using theoretical methods: a technological review" by De Lorenzo A, Andreoli A, Matthie J, Withers P., J Appl Physiol. 1997. 82:1542-1558) normalized by percentage unit of fat mass (FM). It can be seen from FIG. 1 that there is an approximate linear relationship between the chest circumference and measured resistance, which suggests that a quantitative assessment of lung fluid content could be obtained using bio-impedance measurements that are adjusted for the chest circumference of the subject.

A similar finding was observed by analyzing the relationship between the average $R_{EXT}$ and the size of a chest belt having textile electrodes carried thereon that is used to measure trans-thoracic bio-impedance in heart failure patients. The size of the chest belt used (and thus the linear distance between the BIS electrodes) was generally proportional to the chest circumference of the patient. FIG. 2 is a graph showing the effect of chest belt size and therefore the linear distance between BIS electrodes and the average external resistance measured in patients with heart failure. In FIG. 2, four sizes of chest belt (medium—M, large—L, extra large—XL and extra extra large—XXL) are grouped into two sets, and it can be seen that the mean $R_{EXT}$ is higher for the larger chest belt set than the smaller chest belt set, regardless of fat mass and body composition. Indeed, the larger the chest circumference (and thus the larger the linear distance between the bio-impedance measuring electrodes) the higher the impedance of the measured tissue.

Therefore, a quantitative assessment of fluid in the body of a subject (in particular in the lungs of the subject) using bio-impedance measurements is provided that takes into account the chest size of the subject and the distance between the electrodes used to measure the bio-impedance across the chest tissue.

In particular, according to a first aspect of the invention, there is provided a method for estimating the volume of fluid in part of the body of a subject, the method comprising obtaining a measurement of the circumference, c, of the part of the body of the subject; obtaining a measurement of the impedance of the part of the body of the subject using electrodes attached across the part of the body of the subject; and estimating the volume of fluid in the part of the body of the subject from the measurement of impedance and the measurement of the circumference c.

Preferably, the step of obtaining a measurement of the circumference c comprises obtaining the measurement of the circumference c using a circumference sensor placed around the part of the body of the subject. This allows the circumference measurement to be obtained automatically without any action being taken by the subject.

In some embodiments, the step of obtaining a measurement of the circumference c comprises obtaining a plurality of measurements of the circumference using a circumference sensor placed around the part of the body of the subject, and averaging the plurality of measurements to provide the measurement of the circumference c. This averaging, particularly in the case where the measurement is a measurement of the circumference of the chest of the subject, allows the effects of changes in the circumference over time due to breathing to be taken into account.

In an alternative, less preferred, embodiment, the step of obtaining a measurement of the circumference c can comprise receiving a measurement of the circumference c made by the subject or other user.

In some embodiments, the step of estimating the volume of fluid in the part of the body of the subject from the measurement of impedance and the measurement of the circumference c further uses the distance d measured between the electrodes across the skin of the subject.

In preferred embodiments, the distance d is predetermined. This is the case, where, for example, the electrodes are attached or integrated into a harness or other item of clothing which means that the distance between the electrodes is fixed.

In alternative embodiments, the method further comprises the step of obtaining a measurement of the distance, d, between the electrodes across the skin of the subject. Optionally, the step of obtaining a measurement of the distance, d, between the electrodes across the skin of the subject can comprise receiving a measurement of the distance d made by the subject or other user. However, the step of obtaining a measurement of the distance, d, between the electrodes across the skin of the subject preferably comprises obtaining a measurement of the distance d using a sensor. This allows the distance measurement to be obtained automatically without any action being taken by the subject.

The step of obtaining a measurement of the impedance of the part of the body of the subject preferably comprises applying an alternating current across the part of the body of the subject and measuring the potential. Preferably, the step of obtaining a measurement of the impedance of the part of the body of the subject comprises applying alternating current at a plurality of frequencies across the part of the body of the subject and measuring the potential at each frequency. This allows the components of impedance due to extra-cellular fluid and intra-cellular fluid to be separately determined.

In preferred embodiments, the step of estimating the volume of fluid comprises evaluating:

$$V_{EXT} = \left( \rho_{EXT} \frac{A^{1/2} \left( \frac{c}{\pi} \sin\left(\frac{d}{c}\pi\right) \right)^{5/2}}{R_{EXT}} \right)^{2/3}$$

where $V_{EXT}$ is the volume of extra-cellular water in the part of the body, $R_{EXT}$ is the component of the impedance measurements corresponding to the extra-cellular fluid, A is the cross-sectional area of an electrode and $\rho_{EXT}$ is the resistivity of the extra-cellular water.

Preferably, the part of body is the lungs of the subject, the circumference c is the circumference is circumference of the chest of the subject, and the volume of fluid is the volume of extra-cellular fluid in the lungs of the subject.

According to a second aspect of the invention, there is provided a computer program product, comprising computer readable code embodied therein, the computer readable code being configured such that, on execution by a suitable computer or processor, the computer or processor performs the method described above.

According to a third aspect of the invention, there is provided an apparatus for estimating the volume of fluid in a part of the body of a subject, the apparatus comprising a control unit configured to obtain a measurement of the circumference, c, of the part of the body of the subject; obtain a measurement of the impedance of the part of the body of the subject using electrodes attached across the part of the body of the subject; and estimate the volume of fluid in the part of the body of the subject from the measurement of impedance and the measurement of the circumference c.

In preferred embodiments, the apparatus further comprises a circumference sensor that is configured to be placed around the part of the body of the subject and to measure the circumference c of the part of the body of the subject. This allows the circumference measurement to be obtained automatically without any action being taken by the subject.

In some embodiments, the control unit is configured to obtain a plurality of measurements of the circumference using the circumference sensor and to average the plurality of measurements to provide the measurement of the circumference c. This averaging, particularly in the case where the measurement is a measurement of the circumference of the chest of the subject, allows the effects of changes in the circumference over time due to breathing to be taken into account.

In alternative, less preferred embodiments, the control unit is configured to receive an input from the subject or other user indicating the measurement of the circumference c.

In some embodiments, the control unit can be configured to estimate the volume of fluid in the part of the body of the subject from the measurement of impedance, the measurement of the circumference c and a distance d measured between the electrodes across the skin of the subject.

Preferably, the distance d is predetermined. This is the case, where, for example, the electrodes are attached or integrated into a harness or other item of clothing which means that the distance between the electrodes is fixed.

Alternatively, the control unit is further configured to obtain a measurement of the distance, d, between the electrodes across the skin of the subject. In some embodiments, the control unit is configured to receive an input from the subject or other user indicating the measurement of the distance, d. In alternative, preferred embodiments, the apparatus further comprises a sensor for measuring the distance between the electrodes across the skin of the subject. This allows the distance measurement to be obtained automatically without any action being taken by the subject.

The apparatus is preferably configured to apply an alternating current across the part of the body of the subject using the electrodes and to measure the potential. More preferably, the apparatus is configured to apply an alternating current at a plurality of frequencies across the part of the body of the subject and to measure the potential at each frequency. This allows the components of impedance due to extra-cellular fluid and intra-cellular fluid to be separately determined.

Preferably, the control unit is configured to estimate the volume of fluid by evaluating:

$$V_{EXT} = \left( \rho_{EXT} \frac{A^{1/2} \left( \frac{c}{\pi} \sin\left( \frac{d}{c} \pi \right) \right)^{5/2}}{R_{EXT}} \right)^{2/3}$$

where $V_{EXT}$ is the volume of extra-cellular water in the part of the body of the subject, $R_{EXT}$ is the component of the impedance measurements corresponding to the extra-cellular fluid, A is the cross-sectional area of an electrode and $\rho_{EXT}$ is the resistivity of the extra-cellular water.

In preferred embodiments, the part of body is the lungs of the subject, the circumference c is the circumference is circumference of the chest of the subject, and the volume of fluid is the volume of extra-cellular fluid in the lungs of the subject.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
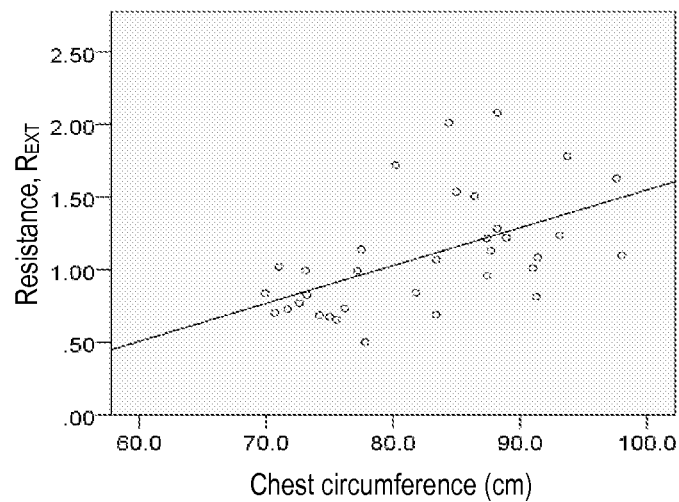
FIG. 1 is a graph showing chest circumference against the resistance determined from bio-impedance measurements for a number of subjects.
Figure 2:
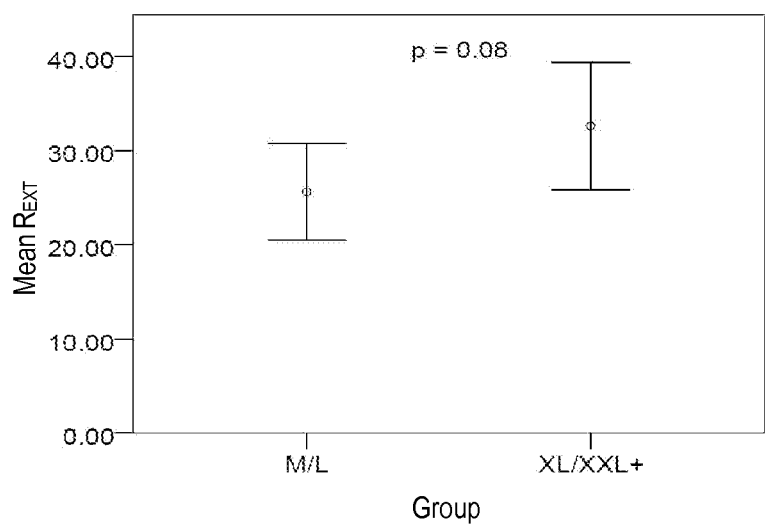
FIG. 2 is a graph showing chest belt size against the average resistance determined from bio-impedance measurements for a number of subjects.
Figure 3:
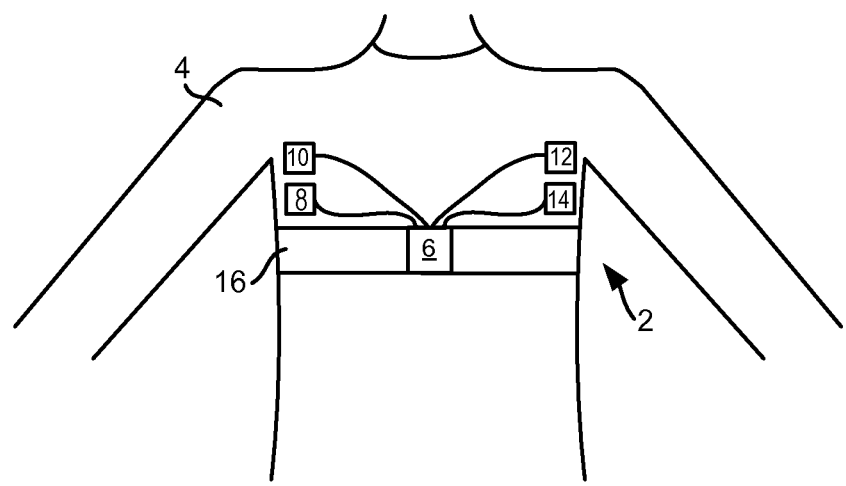
FIG. 3 is an illustration of an apparatus for measuring the fluid content of part of the body of a subject according to an embodiment of the invention.

FIG. 3 shows an apparatus for measuring the fluid content of part of the body of a subject according to an embodiment of the invention. The apparatus 2 is shown in FIG. 3 as being worn by or attached to a subject 4. The apparatus 2 comprises a control unit 6 that is connected to electrodes 8, 10, 12, 14 that are to be attached to, or otherwise placed into contact with, the skin of the subject 4. In the illustrated embodiment, two pairs of electrodes are provided. A first pair of electrodes 8, 12 deliver a small electric current at one or more selected frequencies into the chest of the subject 4.

A second pair of electrodes 10, 14, each placed near a respective one of the electrodes 8, 12 in the first pair, are placed on the skin of the subject 4 to measure the differential potential across the chest of the subject 4. Where, as in the illustrated embodiment, the apparatus 2 is to measure the fluid content of the lungs of the subject 4, the electrodes in each pair are placed on opposite sides of the thorax of the subject 4. The illustrated apparatus 2 is therefore a trans-thoracic bio-impedance measurement system.

Electrodes 8 and 12 form the first pair of electrodes and are used to apply or inject alternating current into the body of the subject 4 and the other pair of electrodes 10 and 14 are used to measure the potential (voltage) across the chest of the subject 4. The frequency of the alternating current applied or injected by the electrode pair 8 and 12 can be varied in steps from a minimum frequency of, for example, 1 kHz, to a maximum of, for example, 1 MHz. Obtaining multiple bio-impedance measurements using currents having different frequencies allows the resistance of extra-cellular water and intra-cellular water to be separately determined, as discussed in more detail below.

In particular, at low measurement frequencies (e.g. approaching 0 Hz) the measured biological tissue impedance is mainly determined by the extracellular fluid content and its characteristics. At these low frequencies, the injected current does not easily pass through cell membranes. At higher frequencies the electrical properties of the biological tissue are determined by both the intracellular and extracellular fluid content as the injected current is able to pass through the cell membranes. Therefore, the influence of the intra- and extra-cellular fluid content on the measured bio-impedance depends on the frequency of the injected current. This allows a characterization of the electrical properties of the biological tissue according to the Cole-Cole model. Using measurements at multiple frequencies allows the approximation by interpolation of the electrical properties of the tissue at direct current (DC, frequency of zero Hz) when the extracellular fluid content is the main component of the impedance.

The potential measured by the second pair of electrodes 10, 14 is processed by the control unit 6 to determine the impedance of the intervening tissue in the body of the subject 4 at the particular frequency of the applied or injected alternating current. The control unit 6 supplies the current at the required frequency to be applied to the subject 4 to the relevant electrodes 8, 12, and receives the measured potential from the second pair of electrodes 10, 14. The control unit 6 can process the measured potential(s) to determine the impedance of the intervening tissue and the fluid content in accordance with the invention. Alternatively, the control unit 6 can transmit the measurements to a remote station (such as a smart phone, laptop computer, desktop computer or other processing device) that processes the measurements to determine the impedance of the tissue and fluid content. This transmission can be performed over wires or using wireless transmission.

Although not shown in FIG. 3, the electrodes 8, 10, 12, 14 are preferably part of or otherwise integrated into an item of clothing, a harness or a chest belt or strap so that they are easy to apply to the subject 4 (this also helps to ensure consistent placement of the electrodes on the subject 4 for multiple measurements of the bio-impedance for a particular subject 4). This also means that the distance between the electrodes in each pair, which is required in determining the fluid content according to the invention, will be known or easily determined. The electrodes 8, 10, 12, 14 can be any type of electrode suitable for making bio-impedance measurements, including textile electrodes.

Alternatively, the electrodes 8, 10, 12, 14 can be 'loose' (i.e. not integrated as a set into a harness or item of clothing) which means that they can be separately applied to the appropriate part of the body of the subject 4. However, in this case it will be necessary to separately determine the distance across the skin of the subject 4 between the electrodes in a pair once they have been applied to the body of the subject 4. This distance can be measured manually by the subject 4 or by a healthcare professional, or it can be automatically measured by a sensor provided in the apparatus 2.

In the illustrated embodiment, the electrodes 8, 10, 12, 14 are connected to the control unit 6 using wires, but it will be appreciated that the electrodes can alternatively be connected wirelessly to the control unit 6. In those embodiments, the control unit 6 can be located remotely from the subject 4.

In addition to the control unit 6 and electrodes 8, 10, 12, 14, as a measurement of the circumference of the part of the body of the subject 4 is required in order to determine the lung fluid content according to the invention, the apparatus 2 preferably further comprises a sensor 16 for measuring the circumference of the part of the body of the subject 4 through which impedance measurements are to be made. In the illustrated embodiment, the sensor 16 is for measuring the circumference of the chest of the subject 4, and is therefore configured in the form of a belt or a strap to be worn around the chest of the subject 4.

The sensor 16 can measure the circumference of the chest of the subject 4 (or any other part of the body of the subject 4) using any of a number of techniques known in the art. For example, the sensor 16 can measure the circumference of the chest of the subject 4 using resistive or inductive principles. Exemplary circumference measuring sensors that use resistive or inductive principles are described in WO 2009/125327. In particular, one way to automatically assess chest circumference could make use of a piezo-resistive sensor built into a textile elastic band that is placed within a wearable vest or that is simply attached to the chest of the subject. The electrical properties of the piezo-resistive band are determined while stretched in a pre-defined length and subsequently compared to the properties obtained while the band is placed around the chest of the subject. The change in electrical properties, given the characteristics of the piezo-resistive material, can be used to determine the length of the band along the chest of the subject, thereby indicating the chest circumference of the subject 4. Similar types of measurement sensors can be used to measure the distance across the skin of the subject 4 between the electrodes. In some cases, a single sensor can be provided for measuring the circumference of the chest and for measuring the distance across the skin of the subject 4.

In alternative, less preferred embodiments, the circumference of the part of the body of the subject 4 can be measured manually by the subject 4 or by a healthcare professional (if they are present when the apparatus 2 is to be used). The manual measurement of the circumference can then be input into the control unit 6 for use in the calculation of the fluid content (in which case the control unit 6 will be provided with a user interface that allows this input).

Although the control unit 6 is shown as being attached to the sensor 16 in FIG. 3, it will be appreciated that in other embodiments the control unit 6 can be separate from the sensor 16. In preferred embodiments, the control unit 6, electrodes 8, 10, 12, 14 and the sensor 16 can be integrated into the same harness or item of clothing as the electrodes 8, 10, 12, 14. Alternative configurations of the control unit 6, electrodes 8, 10, 12, 14 and the sensor 16 will be apparent to those skilled in the art.

According to the Cole-Cole model of biological tissue, the use of applied currents having different frequencies to provide separate measurements of impedance allows the resistance of extra-cellular and intra-cellular water, respectively $R_{EXT}$ and $R_{INT}$, to be determined. From these measurements the volume of fluid occupying the extra-cellular compartment of the measured tissue can be obtained according to the definition of resistivity of a given material, which is:

$$\rho = R \cdot \frac{A}{L} \quad (1)$$

$$R = \rho \cdot \frac{L}{A} \cdot \frac{L}{L} = \rho \cdot \frac{L^2}{V} \quad (2)$$

where $\rho$ is the resistivity of the measured tissue, R is the measured resistance, L is the straight-line distance between the electrodes in a pair when the electrodes are attached to the subject 4, A the area of the section invested by the injected current (e.g. the cross-sectional area of an electrode 8, 10, 12, 14), and V is the volume of the tissue invested by the injected current (with V=A×L).

Figure 4:
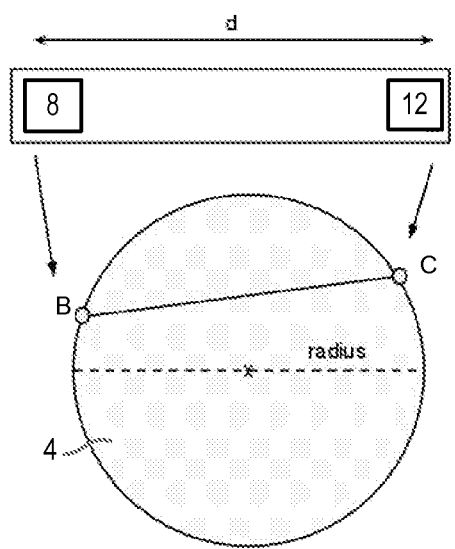
FIG. 4 shows a representation of a possible geometry of a volume of tissue V invested by current applied at a point A on the chest of a subject by an electrode, with a measuring electrode being located at a point B on the chest of the subject.

FIG. 4 shows a representation of a possible geometry of the volume of tissue V invested by current applied at a point B on the chest of the subject 4 by electrode 8, with the measuring electrode 12 being located at a point C on the chest of the subject 4. The chest of the subject 4 is represented as a circle having a radius r. The current injecting electrode 8 and measuring electrode 12 are located a distance d apart when measured over the surface of the chest of the subject 4. Thus, the distance L in equation (2) is the length of the chord from point B to point C.

According to the Cole-Cole model, at low frequencies (approximately 0 Hz), only the extra-cellular water will be conducting current. Therefore, R in equation (1) will be equal to $R_{EXT}$, while p can be derived according to the Hanai theory from the proportion of conducting and non-conductive tissue in the volume of interest (Tetsuya Hanai, Naokazu Koizumi, Takeo Sugano and Rempei Gotoh, Dielectric properties of emulsions II. Electrical conductivities of O/W emulsions COLLOID & POLYMER SCIENCE. Volume 171, Number 1 (1960), 20-23) as follows:

$$\rho = \frac{\rho_{EXT}}{\left(1 - \frac{V_{EXT}}{V}\right)^{3/2}} \quad (3)$$

where $\rho_{EXT}$ is the resistivity of the extra-cellular water (as it is the only portion of the tissue conducting at very low frequencies), while $V_{EXT}$ is the volume of the extra-cellular water.

By combining equations (2) and (3), it is possible to derive the volume of the extra-cellular water as $$V_{EXT} = \left(\rho_{EXT} \frac{V^{1/2} L^2}{R_{EXT}}\right)^{2/3} \quad (4)$$

$\rho_{EXT}$ can be considered equal to the resistivity of saline solution (0.4 Ωm) or, alternatively, the value can be derived from experiments. Such trials can give a value for $\rho_{EXT}$ as 0.403 Ωm for men and 0.423 Ωm for women.

Thus, equation (4) indicates how to determine the volume of the extra-cellular fluid in the thoracic region, $V_{EXT}$, which is responsible for the formation of pulmonary congestion and interstitial and alveolar oedema, from measurements of resistance, the volume V of the tissue affected by the injected current, and the distance L between the injecting and measurement electrodes 8, 12. The latter two parameters are highly patient specific and therefore a measurement of the circumference of the chest of the subject 4 is performed to determine the values of V and L.

It can be seen from FIG. 4 that the distance between the electrodes 8, 12 through the tissue L can be determined from the arc length between the electrodes 8, 12 (and the arc BC equals 'd') and the chest circumference (the circumference of the circular shape representing a cross-section through the chest of the subject 4). The length L (chord length BC) can be found according to the following equation:

$$L = \frac{c}{\pi} \sin\left(\frac{d}{c}\pi\right) \quad (5)$$

where c is the measured chest circumference (which, according to the approximation shown in FIG. 4, is equal to 2·x the radius, r), d is the linear distance between the electrodes.

V=A×L, and A can be assumed for simplicity as the surface area of the electrode 8 that injects current into the tissue, although it will be appreciated by those skilled in the art that there are alternative ways to determine A. For example, A could be determined using a computer simulation of the expected region of the thorax to be invested by the injected current.

From the above, the volume of the extra-cellular water, $V_{EXT}$, can be obtained as a function of bio-impedance measurements, $R_{EXT}$, the distance between the electrodes along the surface of the chest, d (if this is variable, which in some embodiments it is not) and the measurements of the chest circumference, c, using:

$$V_{EXT} = \left(\rho_{EXT} \frac{A^{1/2}\left(\frac{c}{\pi}\sin\left(\frac{d}{c}\pi\right)\right)^{5/2}}{R_{EXT}}\right)^{2/3} \quad (6)$$

Using this equation, it is possible to calculate the ratio between $V_{EXT}$ and V to derive the hydration rate of the pulmonary tissue, as well as determining changes in fluid accumulation in the lung through monitoring the bio-impedance and chest circumference over time.

It will be appreciated that in embodiments where the distance between the injecting and measuring electrodes 8, 12 is fixed (e.g. the electrodes are integrated into an item of clothing or a strap), the distance d will be known. In alternative embodiments where the distance between the injecting and measuring electrodes 8, 12 is not fixed, d is a variable that needs to be determined in order to calculate the volume of extra-cellular water. As indicated above, this distance d can be measured manually by the subject 4 or healthcare professional, or automatically by a sensor present in the apparatus 2.

It will be appreciated that, in alternative embodiments where measurements of bio-impedance are taken using current at a single frequency, it is not possible to separately determine the components of intra- and extra-cellular fluid content in the measured bio-impedance. However, such a measurement can be used to determine the total fluid content of a part of the body of the subject 4. Those skilled in the art will appreciate that the total fluid content can be derived from equations (2) and (5) above with a suitable model for the resistivity ρ.

In the above equations, the volume of the body of the subject 4 through which the injected current passes is assumed to be a cylinder with cross-section A. It will be appreciated that alternative assumptions can be made about the volume through which the current passes. For example, the volume might be assumed to have a non-uniform cross-section, and/or it might be assumed to follow a curved path through the body of the subject 4. In such cases, the equation for length L will be modified accordingly.

It will also be appreciated that the determination of the volume of the lung fluid content given by equation (6) can potentially be improved by using an elliptical model of the chest of the subject 4 rather than the circular model illustrated in FIG. 4. In such a case, equation (5) will be replaced with a suitable equation for determining chord lengths in ellipses.

Figure 5:
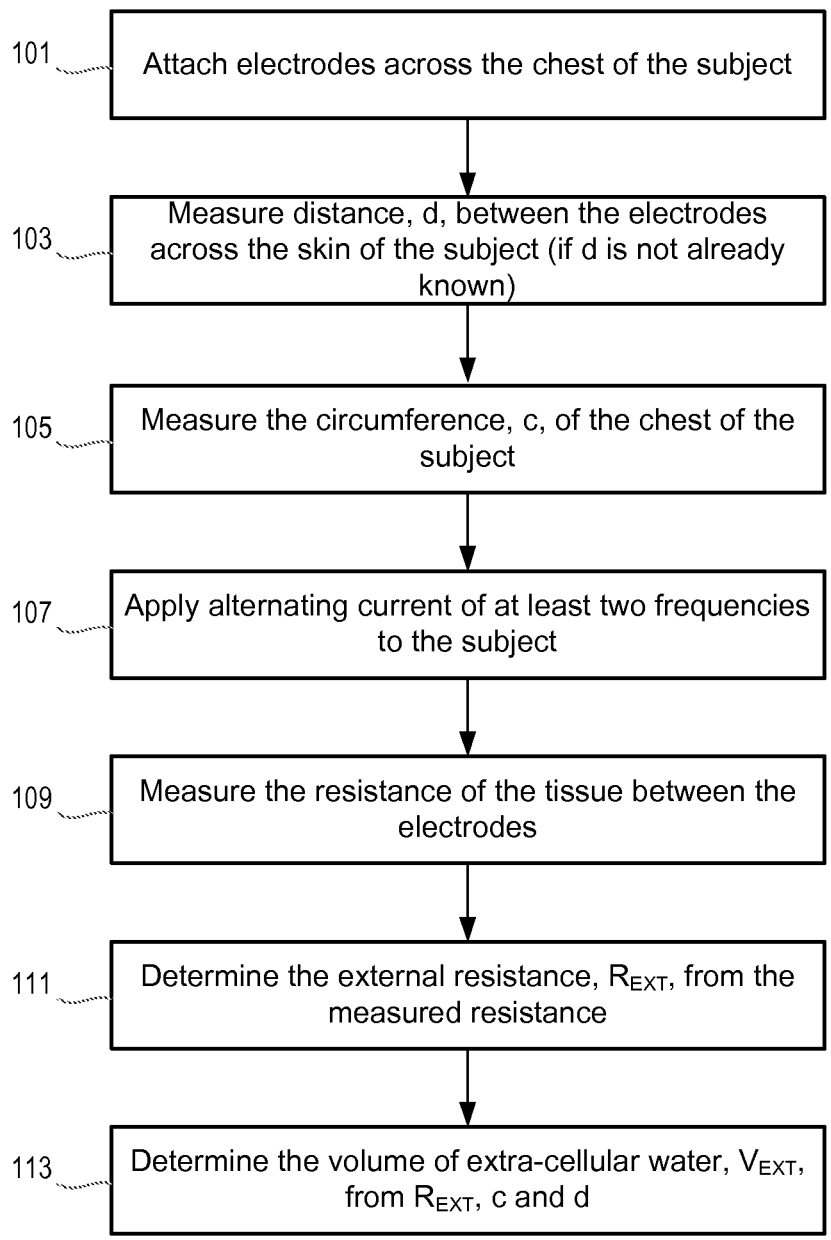
FIG. 5 is a flow chart illustrating a method of estimating the fluid content of the lungs from bio-impedance measurements according to an embodiment of the invention.

A method of determining the volume of extra-cellular water in the lungs of a subject 4 according to an embodiment of the invention is shown in FIG. 5.

In step 101, at least one pair of electrodes 8, 10, 12, 14 is attached to the subject 4. One of the electrodes 8 in the pair is used to inject alternating current into the subject 4 and is placed on one side of the chest of the subject 4. The other electrode 12 in the pair is used to measure the voltage on another part of the chest of the subject 4.

In step 103, the distance d between the electrodes 8, 12 across the skin of the subject 4 is measured (if the distance d is not otherwise already known—for example if the electrodes 8, 12 are integrated into a harness in a way that does not allow the distance between them to be adjusted). The measurement of d can be done using a sensor, as suggested above, or manually by the subject 4 or another person, such as a healthcare professional. Where the measurement is performed manually, the measurement is input into the control unit 6 (or any other unit, such as a remote terminal, that is to perform the calculation of the lung fluid content from the measurements) for use in determining the fluid content of the lungs of the subject 4. In the case where the distance d between the electrodes across the skin of the subject 4 is already known, the value of d will have previously been input to the control unit 6 or other unit.

In step 105, the circumference c of the chest of the subject 4 is measured. As described above, the circumference c is preferably measured using a sensor 16 placed around the chest of the subject 4. The measurement of the circumference is input to the control unit 6. Alternatively, the circumference of the chest of the subject 4 can be measured manually by the subject 4 or another person. In this case, the measured value for c will be manually input to the control unit 6 or other unit.

As the circumference c of the chest of the subject 4 will change as the subject 4 breathes, multiple measurements of the chest circumference can be taken through the breathing cycle and the measurements averaged to give the value of c to be used in determining the lung fluid content.

It will be appreciated that steps 103, 105 and 107 can be performed substantially at the same time or alternatively in any order.

In step 107, alternating current at a first frequency is applied to the subject 4 through the injecting electrode 8. Alternating current at a second frequency is also applied to the subject 4 through the injecting electrode 8 or through another injecting electrode 10.

In step 109, the bio-impedance of the tissue in the chest of the subject 4 between the electrodes 8, 12 at the particular frequency of the applied or injected alternating current is determined from the potential (voltage) measured by the measuring electrode 12.

In step 111, the external resistance, $R_{EXT}$ (the resistance of the extra-cellular fluid), is determined from the bio-impedances of the tissue in the chest measured at the two current frequencies. As described above, the external resistance is preferably determined using the Cole-Cole model.

Then, in step 113, the volume of extra-cellular fluid, $V_{EXT}$, in the chest of the subject 4 (in particular in the volume of tissue between the injecting and measuring electrodes 8, 12) is estimated from $R_{EXT}$, the measured circumference c and the distance d between the electrodes 8, 12. As described above, $V_{EXT}$ is preferably determined according to equation (6).

Once the volume of extra-cellular fluid, $V_{EXT}$, has been estimated, the fraction of tissue comprising fluid can be determined by calculating the ratio between $V_{EXT}$ and V. This can then be used to estimate the total fluid content of the lungs, and thereby provide an indication of the risk or severity of pulmonary oedema. It will also be appreciated that any of the volume of extra-cellular fluid, $V_{EXT}$, the fraction of tissue comprising fluid and the estimate of total fluid content of the lungs can be compared to previously-obtained values in order to determine the progression of the subject 4 from the previous measurement or measurements.

Although the invention has been described above as being primarily for use in determining the volume of extra-cellular water in the lungs of a subject 4, it will be appreciated that the invention can be used for determining the fluid content (whether extra-cellular, intra-cellular or combined) of other parts of the body of the subject 4. For example, an apparatus 2 can be provided for use on the wrist, ankle or other joint of a subject 4 (for example as part of an assessment of inflammation of the joint), in which case the electrodes 8, 10, 12, 14 will be placed on opposite sides of the wrist, ankle or joint and the sensor 16 will measure the circumference as part of the calculation of the distance between the electrodes through the part of the body of the subject 4.

There is therefore provided a method and apparatus that allow a quantitative assessment of fluid in a part of the body of a subject (such as the lungs of the subject) to be made using bio-impedance measurements.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method performed by a processor for estimating a volume of extra-cellular fluid in a part of a body of a subject, the method comprising:
   controlling a set of electrodes to apply a first current of a first frequency to the subject;
   measuring a first resistance in response to application of the first current;
   controlling the set of electrodes to apply a second current of a second frequency to the subject;
   measuring a second resistance in response to application of the second current;
   interpolating a third resistance as a third frequency approaches 0 Hz, the third resistance being associated with the third frequency, the interpolating being based on the first resistance and the second resistance;
   receiving a measurement of a circumference of the part of the body of the subject;
   computing a through-body distance through the body of the subject between a first electrode of the set of electrodes and a second electrode of the set of electrodes based on the circumference; and
   estimating the volume of extra-cellular fluid in the part of the body of the subject based on the interpolated third resistance and the computed through-body distance.

2. The method of claim 1, wherein the step of receiving a measurement of the circumference of the body part of the subject comprises:
   receiving a measured electrical value from a belt placed around the part of the body of the subject; and
   computing the circumference based on the measured electrical value.

3. The method of claim 1, further comprising:
   receiving a measurement of an over-body distance over the exterior of the body of the subject between the first electrode the second electrode,
   wherein the step of computing the through-body distance comprises computing the length of a chord through the circumference for an arc defined by the over-body distance.

4. The method of claim 1, wherein the third frequency is approximately 0 Hz.

5. The method of claim 1, wherein the step of estimating a volume of fluid comprises evaluating $$V_{EXT} = \left( \rho_{EXT} \frac{A^{1/2} L^{5/2}}{R_{EXT}} \right)^{2/3}$$

where $V_{EXT}$ is the volume of fluid, $\rho_{EXT}$ is a resistivity of extracellular fluid, A is a surface area of an electrode of the set of electrodes, L is the through-body distance, and $R_{EXT}$ is the estimated third resistance.

6. The method of claim 1, further comprising:
   determining a gender of the subject;
   selecting a first value as a resistivity value when the gender is male; and selecting a second value as the resistivity value when the gender is female, wherein the step of estimating a volume is further based on the resistivity value.

7. The method of claim 1, wherein:

the step of controlling a set of electrodes to apply a first current of a first frequency to the subject comprises controlling a first electrode of the set of electrodes to apply the first current, and the step of controlling the set of electrodes to apply a second current of a second frequency to the subject comprises controlling a second electrode of the set of electrodes to apply the second current.

8. An apparatus for estimating a volume of extra-cellular fluid in a part of a body of a subject, the apparatus comprising:

a set of electrodes for attachment to the part of the body of the subject; and a processor configured to:

control the set of electrodes to apply a first current of a first frequency to the subject, measure a first resistance in response to application of the first current, control the set of electrodes to apply a second current of a second frequency to the subject, measure a second resistance in response to application of the second current, interpolate a third resistance as a third frequency approaches 0 Hz, the third resistance being associated with the third frequency based on the first resistance and the second resistance, wherein the third frequency is lower than the first frequency and the second frequency, receive a measurement of a circumference of the part of the body of the subject, compute a through-body distance through the body of the subject between a first electrode of the set of electrodes and a second electrode of the set of electrodes based on the circumference, and estimate the volume of extra-cellular fluid in the part of the body of the subject based on the interpolated third resistance and the computed through-body distance.

9. The apparatus of claim 8, further comprising:

a belt sensor configured to be disposed around the part of the body of the subject, wherein, in receiving a measurement of the circumference of the body part of the subject, the processor is configured to:

receive a measured electrical value from the belt sensor, and compute the circumference based on the measured electrical value.

10. The apparatus of claim 8, wherein the processor is further configured to:

receive a measurement of an over-body distance over the exterior of the body of the subject between the first electrode and the second electrode, wherein in computing the through-body distance the processor is configured to compute the length of a chord through the circumference for an arc defined by the over-body distance.

11. The apparatus of claim 8, wherein the third frequency is approximately 0 Hz.

12. The apparatus of claim 8, wherein in estimating a volume of fluid the processor is configured to evaluate $$V_{EXT} = \left( \rho_{EXT} \frac{A^{1/2} L^{5/2}}{R_{EXT}} \right)^{2/3}$$

where $V_{EXT}$ is the volume of fluid, $\rho_{EXT}$ is a resistivity of extracellular fluid, A is a surface area of an electrode of the set of electrodes, L is the through-body distance, and $R_{EXT}$ is the estimated third resistance.

13. The apparatus of claim 8, wherein the processor is further configured to:

determine a gender of the subject;

select a first value as a resistivity value when the gender is male; and select a second value as the resistivity value when the gender is female, wherein, in estimating a volume, the processor is configured to estimate the volume further based on the resistivity value.

14. The apparatus of claim 8, wherein:

the set of electrodes includes a first electrode, a second electrode, a third electrode, and a fourth electrode, wherein in controlling a set of electrodes to apply a first current of a first frequency to the subject the processor is configured to control the first electrode of the set of electrodes to apply the first current, and in controlling the set of electrodes to apply a second current of a second frequency to the subject the processor is configured to control the second electrode of the set of electrodes to apply the second current.

15. A non-transitory machine-readable storage medium encoded with instructions for execution by a processor for estimating a volume of extra-cellular fluid in a part of a body of a subject, the non-transitory machine-readable storage medium comprising:

instructions for controlling a set of electrodes to apply a first current of a first frequency to the subject;

instructions for measuring a first resistance in response to application of the first current;

instructions for controlling the set of electrodes to apply a second current of a second frequency to the subject;

instructions for measuring a second resistance in response to application of the second current;

instructions for estimating a third resistance associated with a third frequency based on the first resistance and the second resistance, wherein the third frequency is lower than the first frequency and the second frequency;

instructions for receiving a measurement of a circumference of the part of the body of the subject;

instructions for computing a through-body distance through the body of the subject between a first electrode of the set of electrodes and a second electrode of the set of electrodes based on the circumference; and instructions for estimating the volume of extra-cellular fluid in the part of the body of the subject based on the interpolated third resistance and the computed through-body distance.

16. The non-transitory machine-readable storage medium of claim 15, wherein the step of receiving a measurement of the circumference of the body part of the subject comprises:

instructions for receiving a measured electrical value from a belt placed around the part of the body of the subject; and instructions for computing the circumference based on the measured electrical value.

17. The non-transitory machine-readable storage medium of claim 15, further comprising:

instructions for receiving a measurement of an over-body distance over the exterior of the body of the subject between the first electrode and the second electrode, wherein the instructions for computing the through-body distance comprise instructions for computing the length of a chord through the circumference for an arc defined by the over-body distance.

18. The non-transitory machine-readable storage medium of claim 15, wherein the third frequency is approximately 0 Hz.

19. The non-transitory machine-readable storage medium of claim 15, wherein the instructions for estimating a volume of fluid comprise instructions for evaluating $$V_{EXT} = \left(\rho_{EXT} \frac{A^{1/2} L^{5/2}}{R_{EXT}}\right)^{2/3}$$

where $V_{EXT}$ is the volume of fluid, $\rho_{EXT}$ is a resistivity of extracellular fluid, A is a surface area of an electrode of the set of electrodes, L is the through-body distance, and $R_{EXT}$ is the estimated third resistance.

20. The non-transitory machine-readable storage medium of claim 15, further comprising:

instructions for determining a gender of the subject;

instructions for selecting a first value as a resistivity value when the gender is male; and instructions for selecting a second value as the resistivity value when the gender is female, wherein the instructions for estimating a volume are further based on the resistivity value.

* * * * *